United States Patent
Nappa et al.

(10) Patent No.: US 6,281,395 B1
(45) Date of Patent: Aug. 28, 2001

(54) 1,1,1,2,3,3,3-HEPTAFLUOROPROPANE MANUFACTURING PROCESS

(75) Inventors: Mario Joseph Nappa, Newark; V. N. Mallikarjuna Rao, Wilmington, both of DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/283,451

(22) Filed: Apr. 1, 1999

Related U.S. Application Data

(60) Provisional application No. 60/080,706, filed on Apr. 3, 1998.

(51) Int. Cl.⁷ .................................................. C07C 17/08
(52) U.S. Cl. ...................................... 570/165; 570/169
(58) Field of Search ................................ 570/165, 169

(56) References Cited

U.S. PATENT DOCUMENTS

| | | | |
|---|---|---|---|
| 4,158,023 | 6/1979 | Von Halasz | 260/653.9 |
| 4,978,649 | 12/1990 | Surovikin et al. | 502/416 |
| 5,036,036 | 7/1991 | Lerou | 502/317 |
| 5,043,491 | 8/1991 | Webster et al. | 570/165 |
| 5,057,634 | 10/1991 | Webster et al. | 570/157 |
| 5,068,472 | 11/1991 | Webster et al. | 570/157 |
| 5,068,473 | 11/1991 | Kellner et al. | 570/176 |
| 5,136,113 | 8/1992 | Rao | 570/176 |
| 5,146,018 | 9/1992 | Kellner et al. | 570/156 |
| 5,399,795 | 3/1995 | Franz et al. | 570/165 |
| 5,563,304 | * 10/1996 | Rao | 570/169 |
| 5,689,019 | 11/1997 | Aoyama et al. | 570/167 |
| 5,705,719 | 1/1998 | Bloos et al. | 570/179 |
| 6,018,083 | 1/2000 | Manogue et al. | 570/156 |

FOREIGN PATENT DOCUMENTS

| | | |
|---|---|---|
| 0 002 098 | 5/1979 | (EP) . |
| 0 539 989 A1 | 5/1993 | (EP) . |
| 902590 | 8/1962 | (GB) . |

OTHER PUBLICATIONS

I.L. Knunyants et al., Addition of Hydrogen Halides to Fluoro Olefins, *Institute of Heteroorganic Compounds,* 9, 1568–1569, Sep., 1960.

Milos Hullicky, Chemistry of Organic Fluorine Compounds, *A Laboratory Manual with Comprehensive Literature Coverage,* pp. 228–229.

* cited by examiner

*Primary Examiner*—Alan Siegel

(57) ABSTRACT

A process is disclosed for the manufacture of $CF_3CHFCF_3$ containing less than 0.01 ppm $(CF_3)_2C=CF_2$. The process involves (a) contacting hexafluoropropene in the vapor phase at a temperature of less than about 260° C. with hydrogen fluoride in the presence of a selected fluorination catalyst or produce a product containing less than 10 parts $(CF_3)_2C=CF_2$ per million parts of $CF_3CHFCF_3$; and (b) treating the product of (a) as necessary to remove excess $(CF_3)_2C=CF_2$. Suitable catalysts include: (i) an activated carbon treated to contain from about 0.1 to about 10 weight % added alkali or alkaline earth metals, (ii) three dimensional matrix porous carbonaceous materials, (iii) supported metal catalysts comprising trivalent chromium, and (iv) unsupported chrome oxide prepared by the pyrolysis of $(NH_4)_2Cr_2O_7$.

20 Claims, No Drawings

1,1,1,2,3,3,3-HEPTAFLUOROPROPANE MANUFACTURING PROCESS

This application claims benefit of provisional No. 60/080,706 filed Apr. 3, 1998.

FIELD OF THE INVENTION

The present invention relates to a synthesis of 1,1,1,2,3,3,3-heptafluoropropane by contacting HF and hexafluoropropylene in the presence of a catalyst.

BACKGROUND 1,1,1,2,3,3,3-Heptafluoropropane (i.e., $CF_3CHFCF_3$ or HFC-227ea) is useful as a fire extinguishant, refrigerant, blowing agent and propellant. It can be prepared by the addition of hydrogen fluoride to hexafluoropropylene. British Patent Specification No. 902,590 claims a process for the manufacture of HFC-227ea by contacting in the vapor phase an equimolar mixture of HF and hexafluoropropylene in the presence of activated carbon at temperatures between 250° C. and 450° C. The reaction temperatures cited in the two examples of this publication were 392 to 402° C. and 300 to 306° C. Various problems are reported associated with operating at such high reaction temperatures including operating safety, corrosion of the construction materials involved and in particular, production of toxic products, especially perfluoroisobutylene (PFIB). U.S. Pat. No. 5,399,795 discloses the manufacture of HFC-227ea by the reaction of HF and hexafluoropropene in the presence of a weakly basic ion exchange resin. U.S. Pat. No. 5,689,019 discloses the same reaction in the presence of an antimony catalyst. Both of these patents suggest that reaction temperatures of less than 120° C. are necessary in order to suppress the formation of PFIB. PFIB removal is addressed in U.S. Pat. No. 5,705,719.

There is a need for a high yield HFC-227ea manufacturing process which does not co-produce even small quantities of PFIB.

SUMMARY OF THE INVENTION

A process is provided for the manufacture of 1,1,1,2,3,3,3-heptafluoropropane containing less than 0.01 ppm $(CF_3)_2C=CF_2$. The process comprises (a) contacting hexafluoropropene in the vapor phase at a temperature of less than about 260° C. with hydrogen fluoride in the presence of a fluorination catalyst selected from the group consisting of (i) an activated carbon treated to contain from about 0.1 to about 10 weight % added alkali or alkaline earth metals, (ii) three dimensional matrix porous carbonaceous materials, (iii) supported metal catalysts comprising trivalent chromium and (iv) unsupported chrome oxide $(Cr_2O_3)$ prepared by the pyrolysis of $(NH_4)_2Cr_2O_7$, to produce a product containing less than 10 parts perfluoroisobutylene per million parts of 1,1,2,3,3,3-heptafluoropropane; and (b) treating the product of (a) as necessary to remove excess perfluoroisobutylene.

DETAILS OF THE INVENTION

This invention provides a process for the preparation of 1,1,1,2,3,3,3-heptafluoropropane (i.e., $CF_3CHFCF_3$ or HFC-227ea) by contacting hexafluoropropylene (i.e., $CF_2=CFCF_3$, or HFP) with anhydrous HF in the presence of selected catalysts. The catalysts used herein are selected to facilitate producing only low levels (i.e., 10 ppm, or less, based on the HFC-227ea produced) of PFIB. This in turn reduces the cost of any further treatment to obtain the desired product having less than 0.01 ppm PFIB (i.e., less than 0.01 parts by weight PFIB per million parts HFC-227ea) in the final product.

Among the suitable catalysts of this invention is treated activated carbon. It is noted that carbon may have alkali and/or alkaline earth metal associated with its inherent ash content. However, in accordance with this invention, added alkali or alkaline earth metal is desirable. Indeed, preferably, a low ash content carbon is used. Preferably, the low ash content carbon is treated with an alkali or akaline earth metal compound selected from lithium, sodium, potassium, rubidium cesium, magnesium, calcium, strontium and/or barium. Potassium is particularly preferred. In accordance with one embodiment of this invention, the carbon used for HFC-227ea preparation contains less than about 0.1 weight percent ash. The low ash content carbon is prepared as described in U.S. Pat. No. 5,136,113 which is incorporated herein by reference. Typically, the low ash content carbon is treated so as to have a total content of from about 0.1 to 10 weight percent of added alkali or alkaline earth metals. The treatment is done using soluble of the metals by procedures well known to those skilled in the art.

The carbons of this invention also include three dimensional matrix porous carbonaceous materials. Examples are those described in U.S. Pat. No. 4,978,649, which is hereby incorporated by reference herein in its entirety. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Other suitable vapor phase fluorination catalysts include certain catalysts comprising trivalent chromium. Examples include supported $CrX_3$, where each X is independently Cl or F. In addition to a catalytically effective amount of trivalent chromium such fluorination catalysts can include other components to increase catalyst activity and/or life such as one or more divalent metal cations (e.g., zinc, magnesium and/or cobalt). The trivalent chromium catalyst may be supported, for example on alumina, aluminum fluoride, fluorided alumina, magnesium fluoride or carbon. Suitable unsupported $Cr_2O_3$ may be prepared by the pyrolysis of $(NH_4)_2Cr_2O_7$ as described in U.S. Pat. No. 5,036,036.

The physical shape of the catalyst is not critical and may, for example, include pellets, powders or granules.

The catalytic hydrofluorination of $CF_3CF=CF_2$ to $CF_3CHFCF_3$ is suitably conducted at a temperature in the range of from about 175° C. to about 260° C., provided that when a carbon is used as the fluorination catalyst, the reaction temperature is less than about 230° C., and preferably from about 200° C. to about 230° C. The contact time is typically from about 1 to about 300 seconds, preferably from about 10 to about 60 seconds. The mole ratio of HF:HFP is typically in the range of 1:1 to 30: 1, and is preferably from 2: 1 to 5:1.

The HFP starting material can be produced by conventional means. However, of particular note is HFP produced (along with HFC-227ea itself) by hydrodechlorination of 2-chloro-1,1,1,2,3,3,3-heptafluoropropane (i.e., $CF_3CClFCF_3$ or CFC-217ba). Further information on production of HFP/CFC-227ea mixtures using CFC-217ba is provided in U.S. patent application No. 60/080,708, the priority document for U.S. patent application Ser. No. 09/283,450 which issued as U.S. Pat. No. 6,018,083.

The reaction pressure can be subatmospheric, atmospheric or superatmospheric.

The process of this invention can be carried out readily in the vapor using well known chemical engineering practice.

Traces of PFIB can be removed by treatment with a solution of hydrogen fluoride and/or hydrogen chloride in methanol at a temperature and pressure at which the methanol solution is liquid. Further details about the PFIB removal treatment can be found in European Patent Application No. 0 002 098 and U.S. Pat. No. 5,705,719. Thus, when necessary in (b), excess PFIB can be removed by sorption or reaction with methanol.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

$CF_3CF=CF_2 + HF \rightarrow CF_3CHFCF_3$

Legend

| | |
|---|---|
| 227ea is $CF_3CHFCF_3$ | CT is contact time |
| AWC is acid washed carbon | NAWC is non-acid washed carbon |
| HFP is $CF_3CF=CF_2$ | 1225zc is $CF_3CH=CF_2$ |
| 218 is $CF_3CF_2CF_3$ | 116 is $CF_3CF_3$ |
| 217ba is $CF_3CClFCF_3$ | 236fa is $CF_3CH_2CF_3$ |
| $C_6F_{12}$ are HFP Dimers | 51–14 is $C_6F_{14}$ |
| 52–13 is $C_6HF_{13}$ | 1224 is $C_3HClF_4$ |
| 161–14 is $C_7F_{14}$ | PFIB is $(CF_3)_2C=CF_2$ |

General Procedure (Exs. 1 to 3). A 15 in. (38.1 cm)×½ in. (1.3 cm) Hastelloy® nickel alloy tube was filled with 2.76 g (5 mL) of 10% KOH/AWC (6–10 mesh), (3.4–2.0 mm)) catalyst in Example 1, 1.58 g (5 mL) of AWC (6–10 mesh), (3.4–1.2 mm)) catalyst in Example 2 and 2.08 g (5 mL) of a commercially available activated carbon (6–16 mesh, (3.4–1.2 mm)) catalyst in Example 3. The HF flow was 15 sccm ($2.5 \times 10^{-7}$ m$^3$/s) and the HFP flow was 5 sccm ($8.3 \times 10^{-8}$ m$^3$/s). The reactor was heated to the temperatures shown in Table 1. The products were analyzed by GC and the results in mole % are shown in Table 1.

TABLE 1

| Example No. | Temp. °C. | CT Sec. | HFP | 227ea | 1225zc | Cat. |
|---|---|---|---|---|---|---|
| 1 | 175 | 14 | 94.4 | 5.5 | 0.1 | KOH/C |
| 2 | 175 | 14 | 95.2 | 4.7 | 0.1 | AWC |
| 3 | 175 | 14 | 97.1 | 2.9 | 0.0 | NAWC |
| 1 | 200 | 14 | 56.8 | 43 | 0.4 | KOH/C |
| 2 | 200 | 14 | 74.7 | 25 | 0.3 | AWC |
| 3 | 200 | 14 | 80.2 | 20 | 0.1 | NAWC |
| 1 | 226 | 14 | 1.2 | 98.4 | 0.4 | KOH/C |
| 2 | 226 | 14 | 7.9 | 91.7 | 0.4 | AWC |
| 3 | 226 | 14 | 42.2 | 57.7 | 0.1 | NAWC |
| 1 | 200 | 28 | 32.2 | 67.1 | 0.6 | KOH/C |
| 2 | 200 | 28 | 50.8 | 49.0 | 0.4 | AWC |
| 3 | 200 | 28 | 64.6 | 35.0 | 0.1 | NAWC |

A sample of the Example 1 product produced at 226° C. was analyzed by GC/mass spectroscopy. The results in area % are shown in Table 2. The HFC-227ea reaction product sample contained no detectable amount of PFIB.

TABLE 2

| Component | Area % |
|---|---|
| 218 | 0.0008 |
| 116 | 0.0065 |
| HFP | 6.6882 |
| 227ea | 92.8065 |
| 1225zc | 0.0053 |
| 217ba/236fa | 0.0381 |
| 1327 | 0.0114 |
| $C_6F_{12}$ | 0.0921 |
| 51–14 | 0.0867 |
| 52–13 | 0.2324 |
| 1224 | 0.0104 |
| $C_9F_{16}$ | 0.0011 |
| 161–14 | 0.0111 |

Comparative Example A

A sample of Calgon PCB non-acid washed carbon (5 mL, 2.65 gm, 12/30 mesh (1.7/0.6 mm)) was activated by heating to 200° C. under a nitrogen flow to remove water. HFP (11.5 sccm, $1.9 \times 10^{-7}$ m$^3$/s) and HF (21.8 sccm, $3.6 \times 10^{-7}$ m$^3$/s) were passed over the carbon catalyst at 425° C. and a sample analyzed by GC/MS is shown in Table A. The temperature was then lowered to 200° C. and sampled again and the results are also shown in Table A. The results are in area % and the detection limit of PFIB is less than 10 ppm.

TABLE A

| | Temperature | |
|---|---|---|
| Component | 200° C. | 425° C. |
| CH4 | 0.02% | 0.1% |
| 23 | — | 0.01% |
| HFP | 70.6% | 3.3% |
| 227ea | 28.9% | 95.0% |
| C6F12 | 0.2% | — |
| PFIB | — | 0.2% |

This comparative example shows the effect of temperature on PFIB production.

Example 4

A 30 mL Hastelloy® nickel alloy tubular reactor was packed with 28.0 g of 12–20 mesh (1.68–0.84 mm) chromium(III) oxide catalyst. The catalyst was prepared by the pyrolysis of $(NH_4)_2Cr_2O_7$ as described in U.S. Pat. No. 5,036,036. The catalyst was activated by heating to 175° C. in a nitrogen flow and then was treated with a 1:1 mixture of HF and $N_2$ at 175° C. for about 0.5 hours. The feed gas was then changed to 4:1 HF:$N_2$ and the reactor temperature was increased to 400° C. over the course of 2 hours and then was held at 400° C. for 0.5 hours. The temperature was then lowered to reaction temperature under a nitrogen flow.

Hexaflouropropylene of 99.99% purity and HF were fed to the reactor under the conditions shown in Table 3. The results of the reaction in mole % are also shown in Table 3.

TABLE 3

| T °C. | Molar Ratio HF:HFP | C.T. Sec. | % HFP | % 227ea |
|---|---|---|---|---|
| 200 | 10:1 | 5 | 86.5 | 13.5 |
| 200 | 10:1 | 15 | 67.6 | 32.3 |
| 200 | 3:1 | 15 | 77.7 | 22.3 |
| 225 | 3:1 | 15 | 43.9 | 56.1 |
| 225 | 10:1 | 15 | 56.5 | 43.5 |
| 225 | 10:1 | 5 | 82.9 | 17.1 |
| 225 | 3:1 | 5 | 76.1 | 23.9 |
| 250 | 3:1 | 15 | 2.2 | 97.8 |
| 250 | 3:1 | 5 | 30.5 | 69.5 |
| 250 | 10 | 15 | 4.6 | 95.4 |
| 250 | 10:1 | 5 | 34.2 | 65.7 |

Example 5

A 30 mL Hastelloy® nickel alloy tubular reactor was packed with 5.13 g of 7.5% $CrCl_3$ on acid-washed carbon. The catalyst was activated by heating to about 300° C. in a nitrogen flow. The reactor temperature was then reduced to 175° C. and the catalyst treated with a 1:1 mixture of HF and $N_2$ for about 1.3 hours. The feed gas was then changed to 4:1 $HF:N_2$ and the reactor temperature was increased to 300° C. over the course of 1.5 hours. The temperature was then lowered to reaction temperature under a nitrogen flow.

Hexafluoropopylene of 99.89% purity and HF were fed to the reactor under the conditions shown in Table 4. The results of the reaction in mole % are also shown in Table 4.

TABLE 4

| T °C. | Molar Ratio HF:HFP | C.T. Sec. | % HFP | % 227ea |
|---|---|---|---|---|
| 200 | 3:1 | 15 | 68.7 | 31.1 |
| 200 | 3:1 | 30 | 44.1 | 55.5 |
| 225 | 3:1 | 15 | 7.4 | 92.2 |
| 225 | 3:1 | 5 | 38.6 | 61.2 |
| 225 | 10:1 | 5 | 25.5 | 74.1 |
| 225 | 10:1 | 15 | 2.0 | 97.6 |
| 250 | 10:1 | 15 | <0.1 | 99.7 |
| 250 | 3:1 | 15 | <0.1 | 99.6 |
| 250 | 3:1 | 5 | 9.3 | 90.4 |
| 250 | 10:1 | 5 | 3.4 | 96.5 |

Example 6

A Hastelloy® nickel alloy tubular reactor was packed with 4.85 g of 7.5% $CrCl_3$ on acid-washed carbon. The catalyst was activated by heating to about 300° C. in a nitrogen flow. The reactor temperature was then reduced overnight under a nitrogen flow to 175° C. and the catalyst treated with a 1:1 mixture of HF and $N_2$ for about 0.2 hours. The feed gas was then changed to 5:1 $HF:N_2$ and the reactor temperature was increased to 325° C. over the course of 1.0 hours. Temperature was then lowered to reaction temperature under a nitrogen flow.

Hexafluoropopylene of 99.90% purity and HF were fed to the reactor under the conditions shown in Table 5. The results of the reaction in mole% are also shown in Table 5.

TABLE 5

| T °C. | Molar Ratio HF:HFP | C.T. Sec. | % HFP | % 227ea |
|---|---|---|---|---|
| 200 | 3:1 | 15 | 41.4 | 58.2 |
| 250 | 3:1 | 15 | <0.1 | 99.7 |

Example 7

A 30 mL Hastelloy® nickel alloy tubular reactor was packed with 5.0 g of a three dimensional matrix porous carbonaceous carbon. The temperature was then lowered to reaction temperature under a nitrogen flow.

Hexafluoropopylene of 99.89% purity and HF were fed to the reactor under the conditions shown in Table 6. The results of the reaction in mole % are also shown Table 6.

TABLE 6

| T °C. | Molar Ratio HF:HFP | C.T. Sec. | % HFP | % 227ea |
|---|---|---|---|---|
| 200 | 3:1 | 15 | 86.4 | 13.6 |
| 200 | 10:1 | 15 | 87.2 | 12.7 |
| 200 | 3:1 | 30 | 75.2 | 24.6 |
| 250 | 3:1 | 15 | 2.9 | 96.8 |
| 250 | 3:1 | 5 | 35.2 | 64.6 |
| 250 | 10:1 | 5 | 28.6 | 71.1 |

What is claimed is:

1. A process for the manufacture of $CF_3CHFCF_3$ containing less than 0.01 ppm $(CF_3)_2C=CF_2$, comprising:
   (a) contacting $CF_2=CFCF_3$ in the vapor phase at a temperature of less than about 260° C. with anhydrous hydrogen fluoride in the presence of a fluorination catalyst selected from the group consisting of (i) an activated carbon treated with a soluble salt of alkali or alkaline earth metals to contain from about 0.1 to about 10 weight % added alkali or alkaline earth metals, (ii) three dimensional matrix porous carbonaceous carbon-carbon composite materials, (iii) supported metal catalysts comprising trivalent chromium, and (iv) unsupported chrome oxide catalysts prepared by the pyrolysis of $(NH_4)_2Cr_2O_7$, to produce a product containing less than 10 parts $(CF_3)_2C=CF_2$ per million parts of $CF_3CHFCF_3$; and
   (b) treating the product of (a) as necessary to remove excess perfluoroisobutylene.

2. The process of claim 1 wherein the catalyst is an activated carbon treated to contain from about 0.1 to about 10 weight % added alkali or alkaline earth metals.

3. The process of claim 1 wherein the catalyst is selected from three dimensional matrix porous carbonaceous materials obtained by introducing a gaseous or vaporous carbon-containing compound into a mass of granules of a carbonaceous material, decomposing the carbon-containing compound to deposit carbon on the surface of the granules, and treating the resulting material with an activator gas comprising steam.

4. The process of claim 1 wherein the catalyst is a supported metal catalyst comprising trivalent chromium.

5. The process of claim 1 wherein the catalyst is an unsupported chrome oxide prepared by the pyrolysis of $(NH_4)_2Cr_2O_7$.

6. The process of claim 1 wherein the $CF_2=CFCF_3$ starting material is produced along with additional $CF_3CHFCF_3$ by hydrodechlorination of $CF_3CClFCF_3$.

7. The process of claim 1 wherein in (b), excess $(CF_3)_2C=CF_2$ is removed by sorption or reaction with methanol.

8. The process of claim 2 wherein the catalyst is an acid-washed carbon treated with KOH.

9. The process of claim 4 wherein the catalyst is a carbon-supported metal catalyst.

10. The process of claim 9 wherein a $CrCl_3$ on acid-washed carbon catalyst is used.

11. A process for the manufacture of $CF_3CHFCF_3$ containing less than 0.01 ppm $(CF_3)_2C=CF_2$, comprising:

(1) activating an unsupported chrome oxide prepared by pyrolyzing $(NH_4)_2Cr_2O_7$ with nitrogen;

(2) treating the activated chrome oxide of (1) with a mixture of nitrogen and HF;

(3) contacting $CF_2=CFCF_3$ in the vapor phase at a temperature of less than about 260° C. with hydrogen fluoride in the presence of said chrome oxide catalyst of (2) to produce a product containing less than 10 parts $(CF_3)_2C=CF_2$ per million parts of $CF_3CHFCF_3$; and (4) treating the product of (3) as necessary to remove excess perfluoroisobutylene.

12. The process of claim 11 wherein the $CF_2=CFCF_3$ starting material is produced by hydrodechlorination of $CF_3CClFCF_3$.

13. The process of claim 11 wherein in (4), excess $(CF_3)_2C=CF_2$ is removed by sorption or reaction with methanol.

14. A process for the manufacture of $CF_3CHFCF_3$ containing less than 0.01 ppm $(CF_3)_2C=CF_2$, comprising:

(A) hydrodechlorination $CF_3CClFCF_3$ to produce $CF_2=CFCF_3$;

(B) contacting said $CF_2=CFCF_3$ in the vapor phase at a temperature of less than about 260° C. with hydrogen fluoride in the presence of a fluorination catalyst selected from the group consisting of (i) an activated carbon treated to contain from about 0.1 to about 10 weight % added alkali or alkaline earth metals, (ii) three dimensional matrix porous carbonaceous materials, (iii) supported metal catalysts comprising trivalent chromium, and (iv) unsupported chrome oxide catalysts prepared by the pyrolysis of $(NH_4)_2Cr_2O_7$, to produce a product containing less than 10 parts $(CF_3)_2C=CF_2$ per million parts of $CF_3CHFCF_3$; and (C) treating the product of (B) as necessary to remove excess perfluoroisobutylene.

15. The process of claim 14 wherein the catalyst is an activated carbon treated to contain from about 0.1 to about 10 weight % added alkali or alkaline earth metals.

16. The process of claim 14 wherein the catalyst is selected from three dimensional matrix porous carbonaceous materials.

17. The process of claim 14 wherein the catalyst is a supported metal catalyst comprising trivalent chromium.

18. The process of claim 14 wherein the catalyst is an unsupported chrome oxide catalyst prepared by the pyrolysis of $(NH4)_2Cr_2O_7$.

19. The process of claim 14 wherein in (C), excess $(CF_3)_2C=CF_2$ is removed by sorption or reaction with methanol.

20. The process of claim 11 wherein in (3) perfluoropropylene is contacted with anhydrous HF.

* * * * *